United States Patent [19]

Goulding

[11] Patent Number: 5,560,864
[45] Date of Patent: Oct. 1, 1996

[54] LIQUID CRYSTALLINE MATERIAL

[75] Inventor: Mark Goulding, Dorset, Great Britain

[73] Assignee: Merck Patent Gesellschaft Mit Beshrankter Haftung, Darmstadt, Germany

[21] Appl. No.: 392,349

[22] Filed: Feb. 22, 1995

[30] Foreign Application Priority Data

Feb. 23, 1994 [EP] European Pat. Off. .............. 94102698

[51] Int. Cl.$^6$ ........................ C09K 19/52; C09K 19/20; C08F 22/00
[52] U.S. Cl. ................. 252/299.01; 252/299.64; 252/299.65; 252/299.66; 252/299.67; 526/318.1; 526/319
[58] Field of Search ............ 252/299.01, 299.61, 252/299.66, 299.63, 299.67, 299.64, 299.65; 359/103, 106; 526/318.1, 319

[56] References Cited

U.S. PATENT DOCUMENTS

| | | | |
|---|---|---|---|
| 5,188,760 | 2/1993 | Hihmet et al. | 252/299.01 |
| 5,210,630 | 5/1993 | Heynderickx et al. | 252/299.01 |
| 5,252,251 | 10/1993 | Sato et al. | 252/299.01 |
| 5,268,783 | 12/1993 | Yoshinaga et al. | 359/103 |
| 5,270,843 | 12/1993 | Wang | 359/106 |
| 5,332,520 | 7/1994 | Bach et al. | 252/299.01 |
| 5,372,745 | 12/1994 | Yoshinaga et al. | 252/299.01 |
| 5,417,884 | 5/1995 | Etzbach et al. | 252/299.61 |

FOREIGN PATENT DOCUMENTS

| | | |
|---|---|---|
| 399279 | 5/1990 | European Pat. Off. . |
| 451905 | 4/1991 | European Pat. Off. . |
| 606940 | 1/1994 | European Pat. Off. . |

*Primary Examiner*—Shean C. Wu
*Attorney, Agent, or Firm*—Millen, White, Zelano, & Branigan, P.C.

[57] ABSTRACT

A liquid crystalline material in the form of an anisotropic gel containing a polymerized monotropic or enantiotropic liquid crystalline material and a low-molecular weight liquid crystalline material, wherein the polymerized material a) forms a permanently oriented network in the low-molecular weight liquid crystalline material b), wherein a) is obtained by (co)-polymerization of a chiral polymerizable compound, and a display cell with such a material. Also, novel bifunctional reactive chiral compounds, novel chiral vinylethers and (co)-polymerizable precursor materials.

14 Claims, No Drawings

LIQUID CRYSTALLINE MATERIAL

The invention relates to a liquid crystalline material in the form of an anisotropic gel containing a polymerized monotropic or enantiotropic liquid crystalline material and a low-molecular weight liquid crystalline material, wherein the polymerized material a) forms a permanently oriented network in the low-molecular weight liquid crystalline material b), characterized in that the polymerized material a) is obtainable by (co)-polymerization of a chiral polymerizable compound.

The invention further relates to a display cell comprising two opposite plates which are transparent to light as the substrate, which plates are provided with an electrode of a material which is transparent to light on the sides facing each other, said electrode carrying an orientation layer and a sealing material being provided between the ends of the plates, a liquid-crystalline material being introduced in the space between the plates and the sealing material which is in the form of, for example, a ring.

BACKGROUND OF THE INVENTION

European Patent Application EP 451,905 discloses a liquid crystalline material in the form of an anisotropic gel comprising a polymerized liquid crystalline material and a low-molecular nematic liquid crystalline material

SUMMARY OF THE INVENTION

In accordance with the invention, a liquid crystalline material as described in the opening paragraph is obtained, wherein polymerized material a) forms a permanently oriented network in the low-molecular weight liquid crystalline material b), characterized in that the low-molecular weight liquid crystalline material exhibits a cholesteric phase. Preferably, said material b) forms a continuous phase around the network of material a).

Preferred embodiments of the invention are:

a) A liquid crystalline material wherein material a) is selected from chiral (meth-)acrylates, epoxy compounds, vinyl ether compounds and thiolene compounds.

b) A liquid crystalline material wherein material a) is a polymerized liquid crystalline material comprising a structure element selected from the formulae 1 to 4:

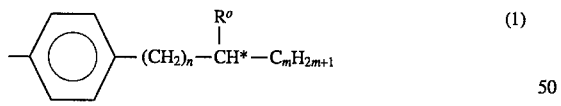

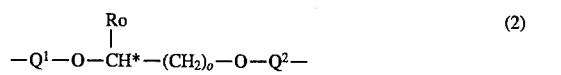

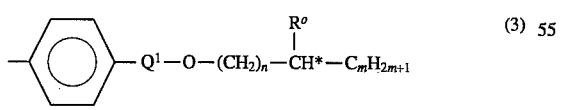

$R^o$ is $CH_3$, $C_6H_5$, F, Cl, CN or $CF_3$,
$Q^1$ and $Q^2$ are each, independently CO or a single bond,
n is 0, 1 or 2,
m is an integer between 1 and 10,
o is 1, 2 or 3, and
* denotes a chiral center.

c) A liquid crystalline material wherein the material b) contains at least one compound of formula II $$R^1\text{—}A^1\text{—}Z^1)_o\text{—}R^2 \qquad \text{II}$$

wherein
$R^1$ and $R^2$ are each independently straight-chained or branched alkyl or alkenyl with 1 to 16 C atoms, 2 to 16 C atoms in the case of alkenyl, in which one or two non-adjacent $CH_2$ groups may be replaced by —O—, —CO—O—, —O—CO— or —O—CO—O—, one of $R^1$ and $R^2$ may also be F, Cl, $CF_3$, $OCF_3$, $OCF_2H$ or CN, $R^1$ is preferably alkyl or alkoxy with 1 to 7 C atoms, and $R^2$ is preferably CN, $A^1$ and $A^2$ are each independently optionally fluorinated 1,4-phenylene in which one or two CH groups may be replaced by N or 1,4-cyclohexylene in which one or two non-adjacent $CH_2$ groups may be replaced by O, preferably 1,4-phenylene optionally substituted by 1–2 F atoms or 1,4-cyclohexylene, $Z^1$ and $Z^2$ are each independently —CO—O—, —O—CO—, —OCH$_2$—, —CH$_2$O—, —CH$_2$CH$_2$—, —C≡C—, —C≡C—C≡C— or a single bond, preferably —CO—O— or a single bond, o is 1, 2 or 3.

d) A liquid crystalline material characterized in that the material a) is obtainable from a chiral, polymerizable compound of the formula I

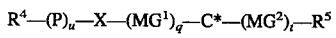

wherein
$R^4$ is $CH_2$=CW—COO—,

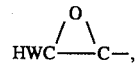

HWN—, CH$_2$=CH—HWC—C—, $CH_2$=CH—O— or HS—CH$_2$-(CH$_2$)$_m$—COO— with W being H, Cl or alkyl with 1–5 C atoms and m being 1–7

P is alkylene with up to 12 C atoms, it being also possible for one or more non adjacent $CH_2$ groups to be replaced by —O—, X is —O—, —S—, —COO—, —OCO— or a single bond, $R^5$ is an alkyl radical with up to 15 C atoms which is unsubstituted, mono- or polysubstituted by halogen, it being also possible for one or more $CH_2$ groups in these radicals to be replaced, in each case independently of one another, by —O—, —S—, —CO—, —OCO—, —CO—O— or —O—CO—O— in such a manner that oxygen atoms are not linked directly to one another, or alternatively $R^5$ has one of the meanings given for $R^4$—(P)$_u$—X—, $MG^1$ and
$MG^2$ are each independently an aromatic ring system or a mesogenic group comprising two or more ring systems optionally linked by bridging groups, C* is an optically active group, preferably selected from the structure elements 2 and 4, above, q and t are each independently 0 or 1, and u is 0 or 1 preferably wherein the material a) is obtainable from a bisacrylate or bisvinylether of formula Ia

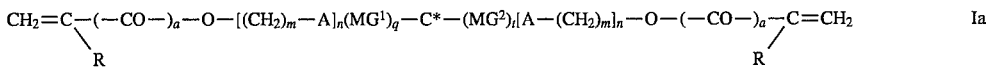

wherein
R is H, $CH_3$ or Cl
A is —O—, —CO—O—, —O—CO— or a single bond
$C^*$ is an optically active group selected from the structure elements 2 and 4, above,
q and t have the meaning given,
a is 0 or 1,
S is an integer of 1 to 6, and
n and m are integers of 0 to 20,
$MG^1$ and
$MG^2$ are selected from

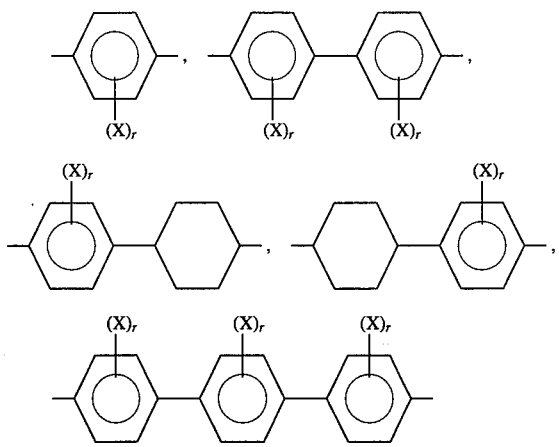

with X being CN or F and r being 0, 1 or 2.

e) A liquid crystalline material wherein the material a) is obtainable by (co)-polymerization of at least one chiral compound selected from the formulae III to V

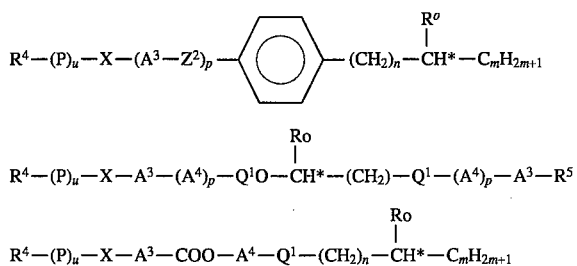

wherein $R^o$, $R^4$, $R^5$, P, X, o, $Q^1$, $Q^2$, n, u and m have the meaning given,
$A^3$ and $A^4$ have the meaning given for $A^1$,
$Z^2$ has the meaning given for $Z^1$ and
p is 0, 1 or 2, in particular wherein material a) is obtainable by polymerization of at least one chiral mesogenic compound, in which
$R^o$ is $CH_3$ or $C_6H_5$.

f) A liquid crystalline material wherein material a) is present in the gel in a quantity of 1–50% by weight, in particular 2–10%.

The invention relates furthermore to a display cell comprising two opposite plates which are transparent to light as the substrate, which plates are provided with an electrode of a material which is transparent to light on the sides facing each other, said electrode carrying an orientation layer and a sealing material being provided between the ends of the plates, a liquid crystalline material being introduced in the space between the plates and the sealing material, wherein the liquid crystalline material is composed of a liquid crystalline material as described above.

Another aspect of the present invention is a copolymerizable precursor material comprising at least one bifunctional reactive achiral compound of formula VI $$R^4\text{—}(P)_u\text{—}X\text{—}MG^1\text{—}X\text{—}(P)_u\text{—}R^4 \qquad \text{VI}$$

wherein $R^4$, X, P and u have the meaning given, and
$MG^1$ is a mesogenic group, and at least one mono reactive chiral compound of formula I, preferably selected from the formulae III to V, preferably a material comprising at least one bifunctional reactive achiral compound of formula VI and at least one reactive chiral compound of formula I in which
$R^4$ is an acrylate radical of formula

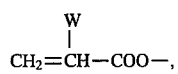

wherein W is H, Cl or alkyl of 1–5 C atoms, or a material comprising at least one compound of formula VI and at least one compound of formula I in which $R^4$ is a vinylether radical of formula $CH_2=CH\text{—}O\text{—}$. Preferred embodiments are:

Copolymerizable material, in which at least one reactive chiral compound of formula I exhibits a structure element of formula 1, in particular with n being 1, $R^o$ being $CH_3$ and m being 2.

The invention relates furthermore to bifunctional reactive chiral compounds of formula I1,

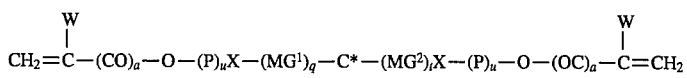

wherein W, P, X, MG$^1$, MG$^2$, a, q, u and t have the meaning given, and

C* is an optically active group and selected from the structure elements 2 and 4; and to chiral polymerizable compounds of formula I2

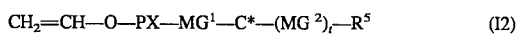

in which P, X, MG$^1$, MG$^2$, C* and t have the meaning given.

Another aspect of the present invention is a cholesteric film obtainable by the steps comprising a) ordering, e.g., aligning on the substrate, the copolymerizable precursor material as described above or a bifunctional reactive chiral compound of formula I1 or I2 in the monomeric state in the presence of a UV initiator and optionally an additive, and b) in situ UV polymerizing the resulting ordered precursor material.

The invention relates furthermore to reactive chiral compounds of formula I3

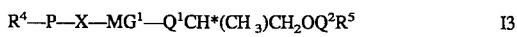

wherein P, X, MG$^1$, Q$^1$, Q$^2$ and R$^5$ have the meaning given and R$^4$ is

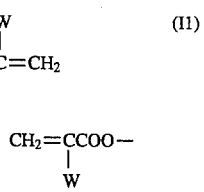

or CH$_2$=CH—O, preferably wherein Q$^1$ and Q$^2$ are single bonds, in particular wherein R$^5$ is alkyl or alkenyl with up to 15 C atoms, particularly 2–15 carbon atoms when alkenyl, wherein R$^3$ and m have the meaning given.

Furthermore, the invention relates to reactive chiral compounds of formula IIIa

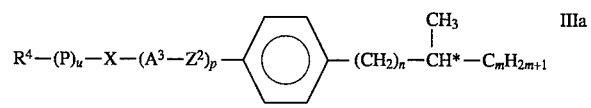

in which R$^4$, P, X, A$^3$, Z$^2$, u and n have the meaning given above, p is 1 or 2, and m is an integer between 2 and 10, in particular wherein m is 2 and n is 1.

Preferred compounds of formula IIIa are those of formulae IIIa1 to IIIa23:

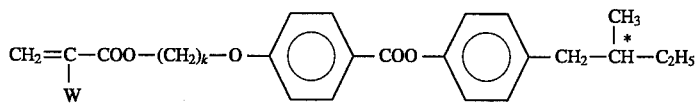

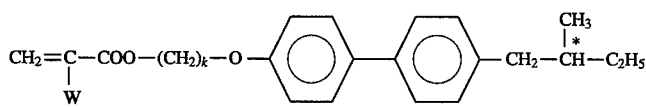

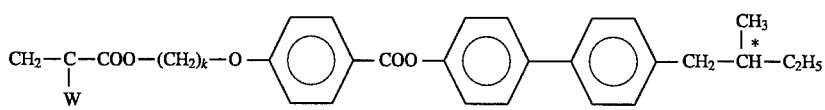

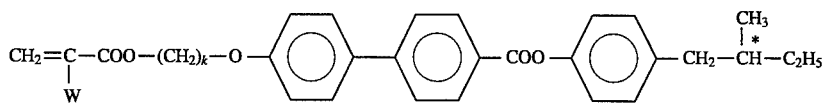

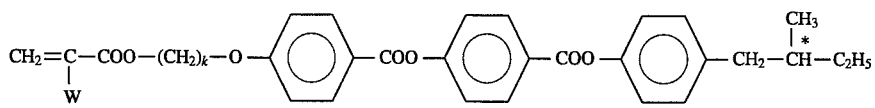

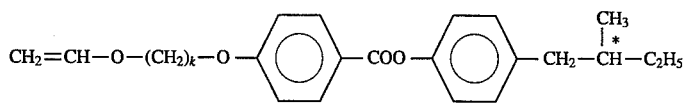

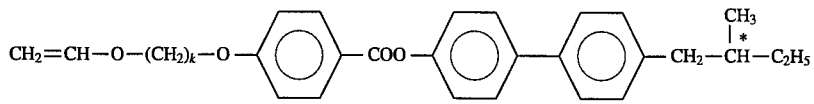

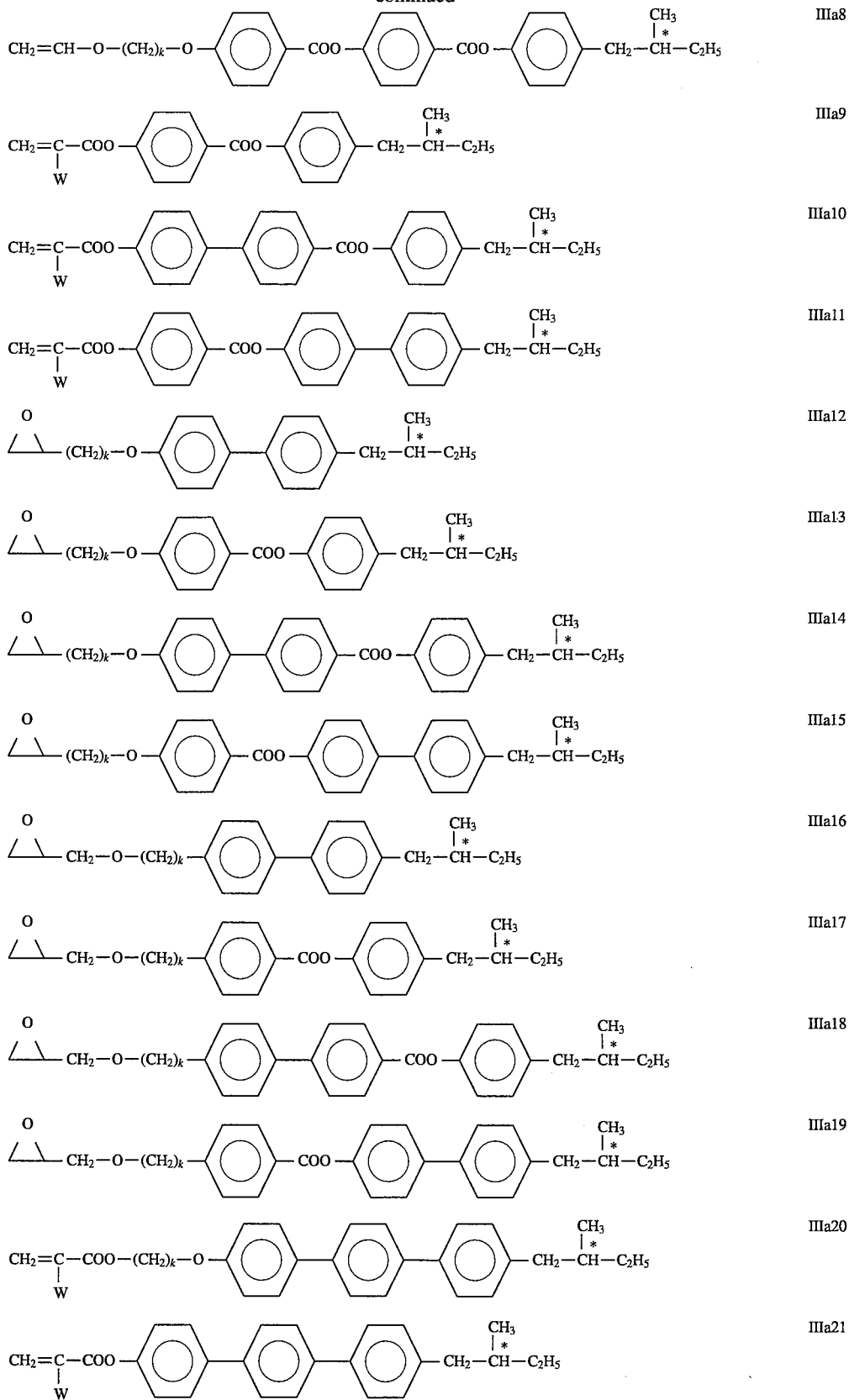

-continued

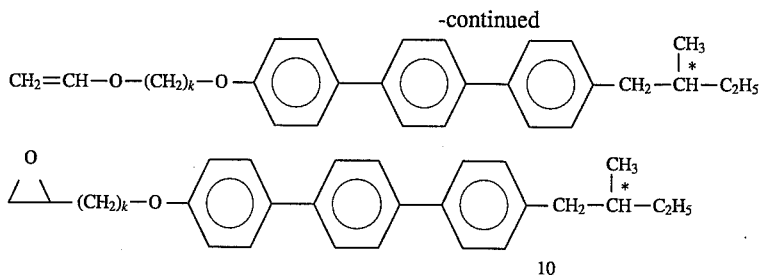
IIIa22

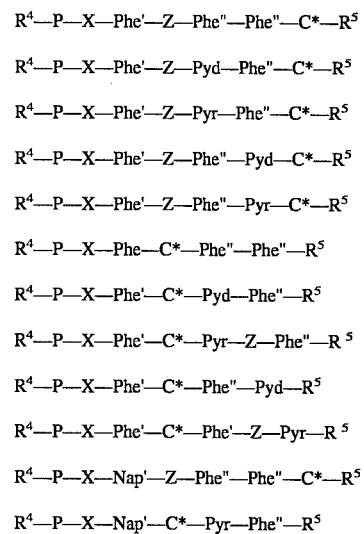
IIIa23 in which W has the meaning given, k is an integer of from 2 to 10, and the phenylene rings are optionally substituted by fluorine, Similar low-molecular mesogenic compounds comprising a structure element selected from the formulae 1 to 4 are known or can be prepared analogously to known procedures, for example, as described in:

1) GB 1 556 994, GB 1 592 161 and GB 1 603 076
2) GB 1 603 076
3) EP 0 168 043
4) WO 94/00 532

Formula I covers chiral reactive liquid crystalline compounds with 2 rings of formulae Ia—Ij $R^4$—P—X—Phe'—Z—Phe—C*—$R^5$     Ia $R^4$—P—X—Phe'—Z—Pyd—C*—$R^5$     Ib $R^4$—P—X—Phe'—Z—Pyr—C*—$R^5$     Ic $R^4$—P—X—Phe'—C*—Phe'—$R^5$     Id $R^4$—P—X—Phe'—C*—Pyd—$R^5$     Ie $R^4$—P—X—Phe'—C*—Pyr—$R^5$     If $R^4$—P—X—Nap'—Z—Phe'—C*—$R^5$     Ig $R^4$—P—X—Nap—Z—Pyd—C*—$R^5$     Ih $R^4$—P—X—Nap—Z—Pyd—C*—$R^5$     Ii R—P—X—Nap—C*—Phe—$R^5$     Ij and compounds with 3 rings of formulae Ik to Iy $R^4$—P—X—Phe'—Z—Phe"—Phe"—C*—$R^5$     Ik $R^4$—P—X—Phe'—Z—Pyd—Phe"—C*—$R^5$     Il $R^4$—P—X—Phe'—Z—Pyr—Phe"—C*—$R^5$     Im $R^4$—P—X—Phe'—Z—Phe"—Pyd—C*—$R^5$     In $R^4$—P—X—Phe'—Z—Phe"—Pyr—C*—$R^5$     Io $R^4$—P—X—Phe—C*—Phe"—Phe"—$R^5$     Ip $R^4$—P—X—Phe'—C*—Pyd—Phe"—$R^5$     Iq $R^4$—P—X—Phe'—C*—Pyr—Z—Phe"—$R^5$     Ir $R^4$—P—X—Phe'—C*—Phe"—Pyd—$R^5$     Is $R^4$—P—X—Phe'—C*—Phe"—Z—Pyr—$R^5$     It $R^4$—P—X—Nap'—Z—Phe"—Phe"—C*—$R^5$     Iu $R^4$—P—X—Nap'—C*—Pyr—Phe"—$R^5$     Iv $R^4$—P—X—Nap'—C*—Pyr—Phe'—$R^5$     Iw $R^4$—P—X—Nap'—C*—Phe"—Pyd—$R^5$     Ix $R^4$—P—X—Nap'—Z—Phe'—Pyr—C*—$R^5$     Iy Wherein $R^4$, $R^5$, P, X and C* have the meaning given, Pyd denotes pyrimidine-2,5-diyl and Pyr denotes pyridine-2,5-diyl.

Z denotes —CO—O—, —O—CO—, —CH$_2$O—, —OCH$_2$—, —CH$_2$CH$_2$—, —C≡C— or a single bond.

In the compounds of formulae Ia–Iy, Phe' denotes a 1,4-phenylene group

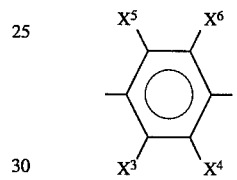

wherein $X^3$–$X^6$ denote independently from each other H or halogen or methyl.

In the compounds of formulae Ia–Iy, Phe" is a 1,4-phenylene group, which is unsubstituted or mono- or polysubstituted by CN or halogen, and in formulae Ig–Ij and Iu–Iy, Nap' is a naphthalene- 2,6-diyl group

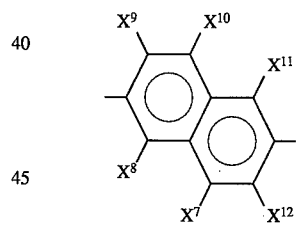

which is unsubstituted or wherein up to 4 of $X^7$–$X^{12}$ are independently from each other halogen while the other denote H.

The compounds of formulae Ia–It are preferred. Especially preferred are the compounds of formulae Ia–If, Ik–It, in particular the compounds of formulae Ia, Id, Ik, Ip and Iq.

In the compounds of formulae Ia–Iy $R^4$ is CH$_2$=CW—COO—, CH$_2$=CH—O—,

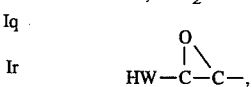

HWN—, HS—CH$_2$—(CH$_2$)$_m$—COO— with W being H, Cl or alkyl with 1–5 C atoms and m being 1–7.

Preferably, $R^4$ is a vinyl ether group, an acrylate group, an amino group or a mercapto group, and especially preferred are the following meanings of $R^4$:

| | |
|---|---|
| $CH_2=CH-COO-$ | $R^4$-1 |
| $CH_2=\underset{\underset{CH_3}{|}}{C}-COO-$ | $R^4$-2 |
| $CH_2=\underset{\underset{Cl}{|}}{C}-COO-$ | $R^4$-3 |
| $CH_2=CH-O-$ | $R^4$-4 |
| $H_2N-$ | $R^4$-5 |
| $H(alkyl)N-$ | $R^4$-6 |
| $HS-CH_2-(CH_2)_m-COO-$ | $R^4$-7 |
| HWC—C— (with O bridging) | $R^4$-8 | with alkyl denoting $C_1-C_3$-alkyl and m being 1–5.

In the compounds of formulae Ia–Iy, the spacer-type group P is alkylene with up to 24 C atoms, it is also being possible for one or more non adjacent $CH_2$ groups to be replaced by O.

In case P is alkylene, P may be straight-chain or branched. P is especially preferred to be ethylene, propylene, butylene, 1-methyl-propylene, 2-methylpropylene, pentylene, 1-methyl-butylene, 2-methyl-butylene, hexylene, 2-ethyl-butylene, 1,3-dimethyl-butylene, heptylene, 1-methylhexylene, 2-methylhexylene, 3-methylhexylene, 4-methylhexylene, 5-methylhexylene, 6-methylhexylene, octylene, 3-ethylhexylene, nonylene, 1-methyloctylene, 2-methyloctylene, 7-methyloctylene, decylene, undecylene, dodecylene, 2-methylundecylene, 2,7,5-trimethyl-nonylene or 3-propylnonylene.

In case P is mono- or polyoxaalkylene, P may be straight-chain or branched. In particular, P is 1-oxa-ethylene, 1-oxapropylene, 2-oxapropylene, 1-oxa-butylene, 2-oxabutylene, 1,3-dioxabutylene, 1-oxa-pentylene, 2-oxa-pentylene, 3-oxy-pentylene, 2-oxa- 3-methyl-butylene, 1-oxahexylene, 2-oxa-hexytene, 3-oxa-hexylene, 1,3-dioxa-hexylene, 1,4-dioxy-hexylene, 1,5-dioxa-hexylene, 1-oxy-heptylene, 2-oxa-heptylene, 1,3-dioxa-heptylene, 1,4-dioxa-heptylene, 1,5-dioxa-heptylene, 1,6-dioxaheptylene, 1,3,5-trioxa-heptylene, 1-oxa-octylene, 2-oxa-octylene, 3-oxaoctylene, 4-oxa-octylene, 1,3-dioxa-octylene, 1,4-dioxa-nonylene, 1,4-dioxa-decylene, 1,4-dioxa-undecylene and 1,3,5-trioxadodecylene.

X is —O—, —S—, —COO—, —OCO— or a single bond and in particular —O—, —COO—, —OCO— or a single bond. In case X is —O—, —S— or —OCO—, the adjacent $CH_2$-group of Q is not replaced by —O—.

Z is preferably —COO—, —OCO—, —$CH_2CH_2$— or a single bond, in particular —CO—O— or a single bond.

$R^5$ can be an alkyl radical with up to 15 C atoms which is unsubstituted, mono or polysubstituted by halogen, it also being possible for one or more $CH_2$ groups in these radicals to be replaced, in each case independently from one another, by —O—, —S—, —CO—, —OCO—, —COO— or —O—COO— in such a manner that oxygen atoms are not linked directly to one another.

If $R^1$, $R^2$, $R^3$ and/or $R^5$ are each independently an alkyl radical or alkoxy radical, it may be straight-chain or branched. Preferably, it is straight-chain, has 2, 3, 4, 5, 6, 7 or 8 carbon atoms and accordingly is preferably ethyl, propyl, butyl, pentyl, hexyl, heptyl, octyl, ethoxy, propoxy, butoxy, pentoxy, hexoxy, heptoxy or octoxy, and furthermore methyl, nonyl, decyl, undecyl, tridecyl, tetradecyl, pentadecyl, methoxy, nonoxy, decoxy, undecoxy, dodecoxy, tridecoxy or tetradecoxy.

If $R^1$, $R^2$, $R^3$ and/or $R^5$ are each independently oxaalkyl, it is preferably straight-chain 2-oxapropyl (=methoxymethyl), 2-oxabutyl (=ethoxymethyl) or 3-oxabutyl (=2-methoxyethyl), 2-, 3- or 4-oxapentyl, 2-, 3-, 4- or 5-oxahexyl, 2-, 3-, 4-, 5- or 6-oxaheptyl, 2-, 3-, 4-, 5-, 6- or 7-oxaoctyl, 2-, 4-, 5-, 6-, 7- or 8-oxanonyl, 2-, 3-, 4-, 5-, 6-, 7-, 8-, or 9-oxadecyl.

Preferred chiral radicals —C*—$R^5$ are each independently, 2-butyl (=1-methylpropyl), 2-methylbutyl, 2-methylpentyl, 3-methylpentyl, 2-ethylhexyl, 2-propylpentyl, 2-octyl, in particular 2-methylbutyl, 2-methylbutoxy, 2-methylpentoxy, 3-methylpentoxy, 2-ethylhexoxy, 1-methylhexoxy, 2-octyloxy, 2-oxa-3-methylbutyl, 3-oxa-4-methylpentyl, 4-methylhexyl, 2-nonyl, 2-decyl, 2-dodecyl, 6-methyloctoxy, 6-methyloctanyloxy, 5-methylheptyloxycarbonyl, 2-methylbutyryloxy, 3-methyivalexyloxy, 4-methylhexanoyloxy, 2-chloropropionyloxy, 2-chloro-3-methylbutyryloxy, 2-chloro-4-methylvaleryloxy, 2-chloro-3-methylvaleryloxy, 2-methyl-3-oxypentyl, 2-methyl-3-oxahexyl, 1-methyoxypropyl-2-oxy, 1-ethoxypropyl- 2-oxy, 1-propoxypropyl-2-oxy, 1-butoxypropyl- 2-oxy, 2-fluoroctyloxy, 2-fluorodecyloxy.

$R^5$ can also have one of the meanings given for $R^4$—P—X— above. In case $R^5$ is an—optionally substituted—alkyl radical, $R^4$ preferably is a vinyl or acrylate group while in case $R^5$ is $R^4$—P—X, all meanings given above for $R^4$ are preferred.

The compounds of formula I are partly novel and partly known, for example from EP 0 399 279 or U.S. Pat. No. 5,252,251.

But these documents deal with ferroelectric liquid crystalline polymers.

There is no hint to materials in which the polymerized material forms a network or to bifunctional reactive chiral compounds nor to chiral vinylether derivatives.

G. Galli, et al. Makromol. Chem. 187, 289–296 (1986) describe a chiral bisacrylate based on 3-methylhexyl-1,6-diol which does not show thermochromic behavior.

The compounds of formula I, wherein C* is a group of formula

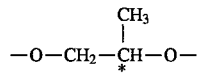

are prepared according to scheme 1 or 2:

Scheme 1

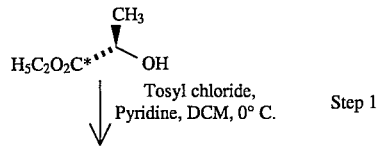

Step 1

5,560,864
-continued
Scheme 1
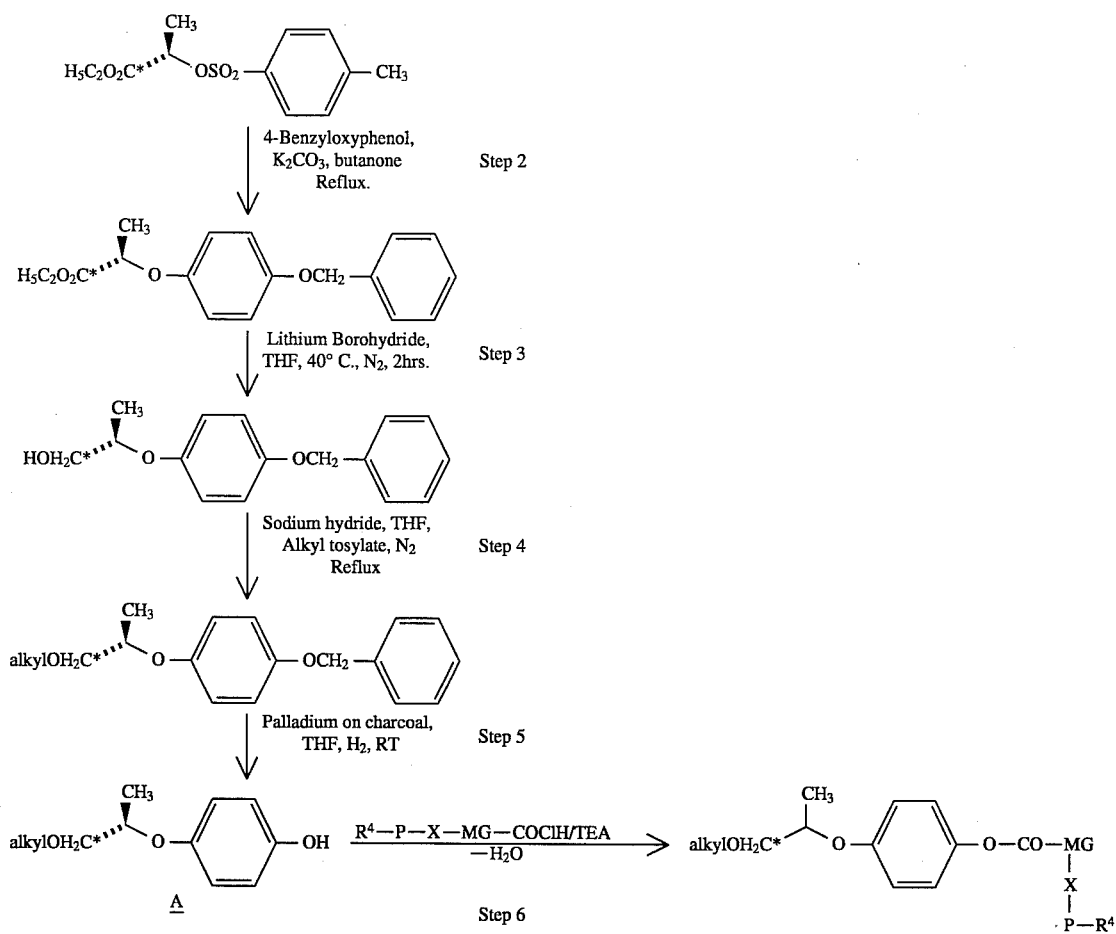
Scheme 2
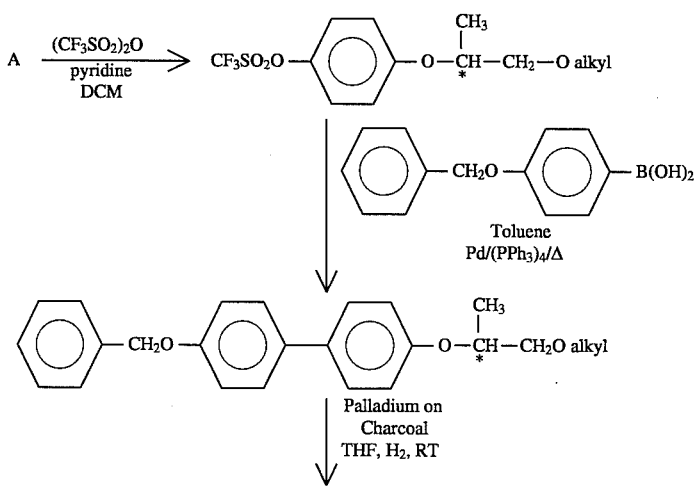

-continued
Scheme 2
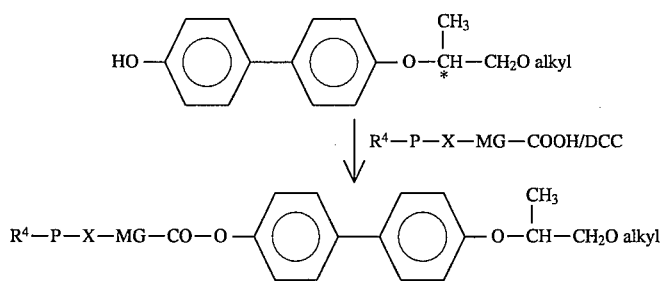
The compounds of formula I, wherein C* is a group of formula
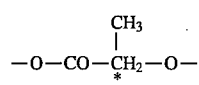
are prepared according to scheme 3 and 4
Scheme 3
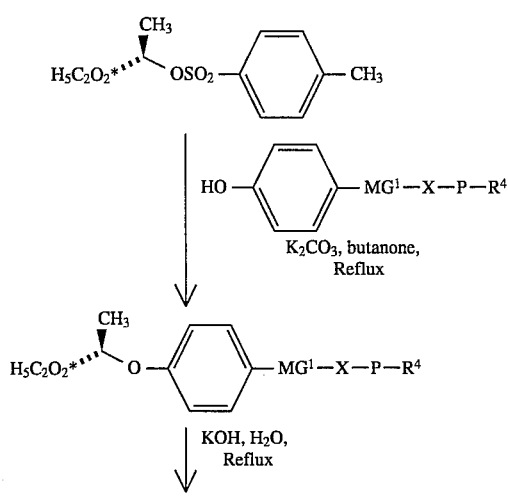
-continued
Scheme 3
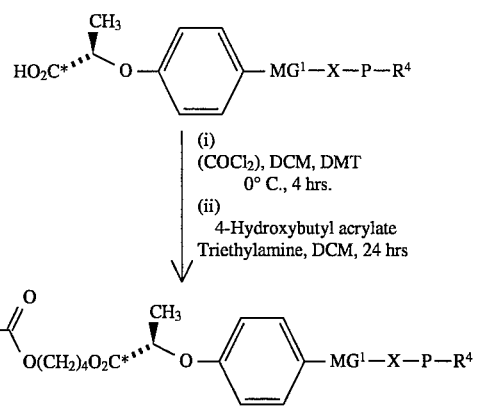
Scheme 4
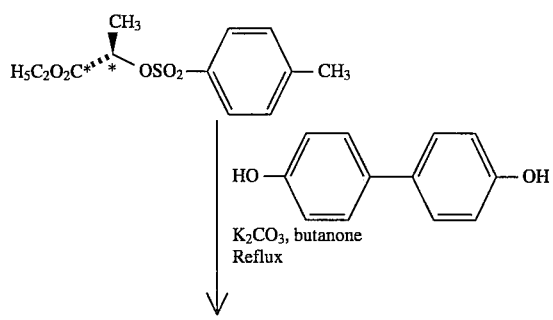

-continued
Scheme 4
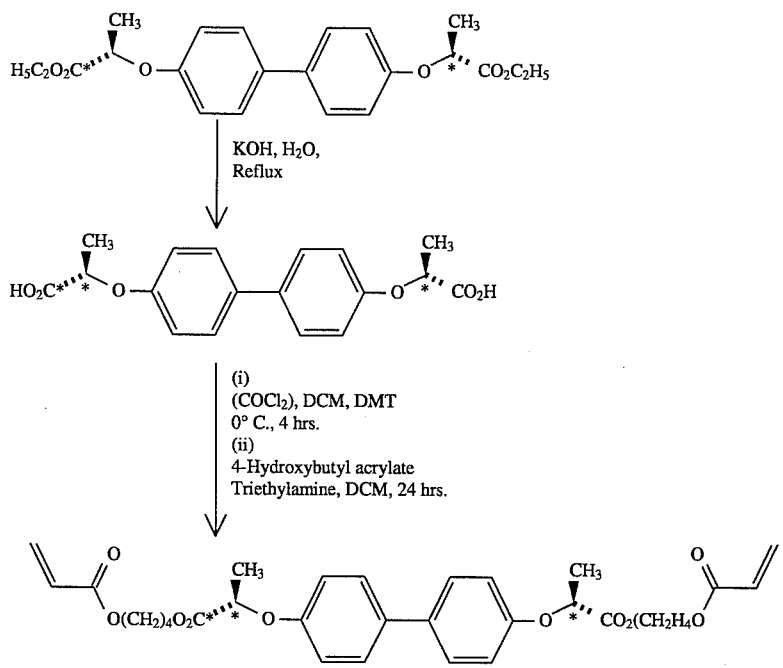
The inventive bifunctional reactive chiral compounds are prepared from the corresponding diols by etherification or esterification with suitable acrylates or vinyl ethers:
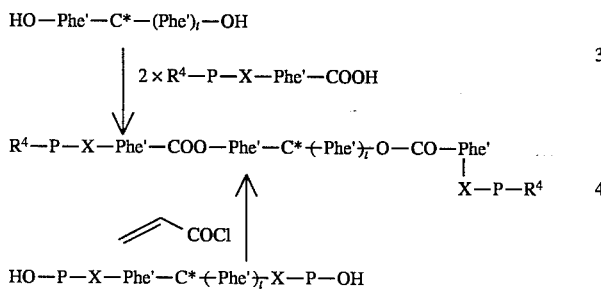
wherein $R^4$, P, X, Phe', C* and t have the meaning given.
The corresponding diols can be prepared according to Scheme 5 to 7:
Scheme 5
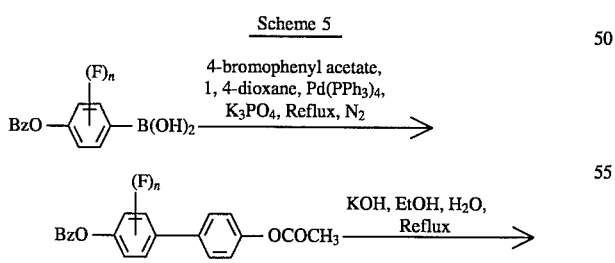
-continued
Scheme 5
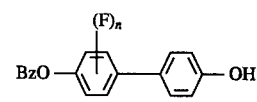
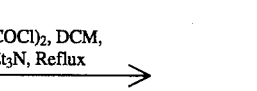
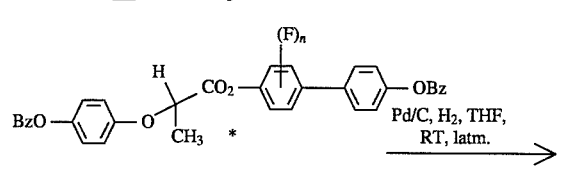
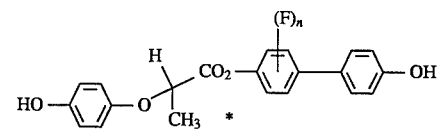

Scheme 6
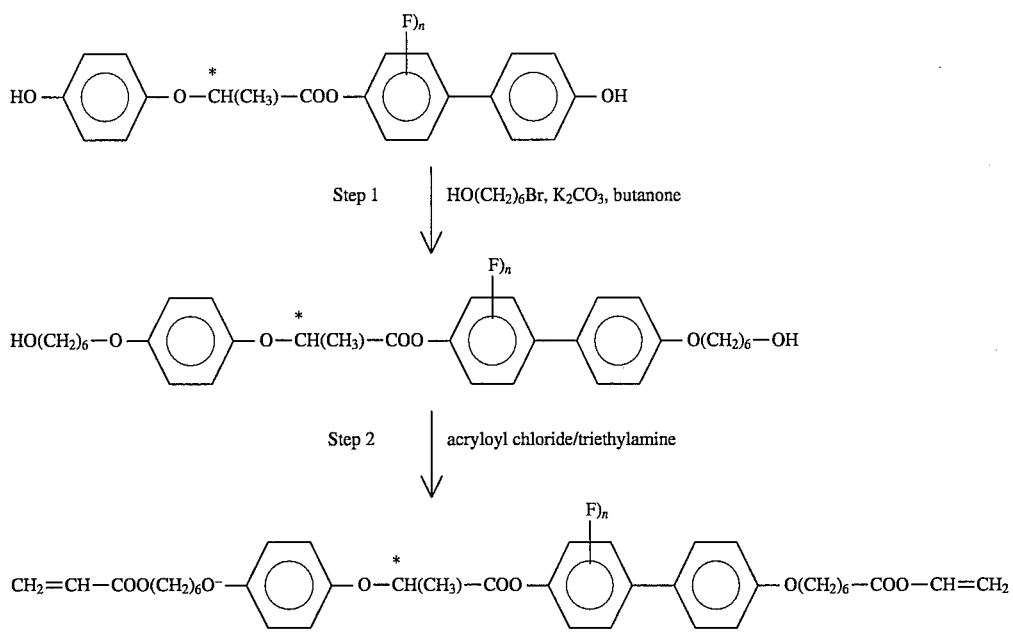
Scheme 7
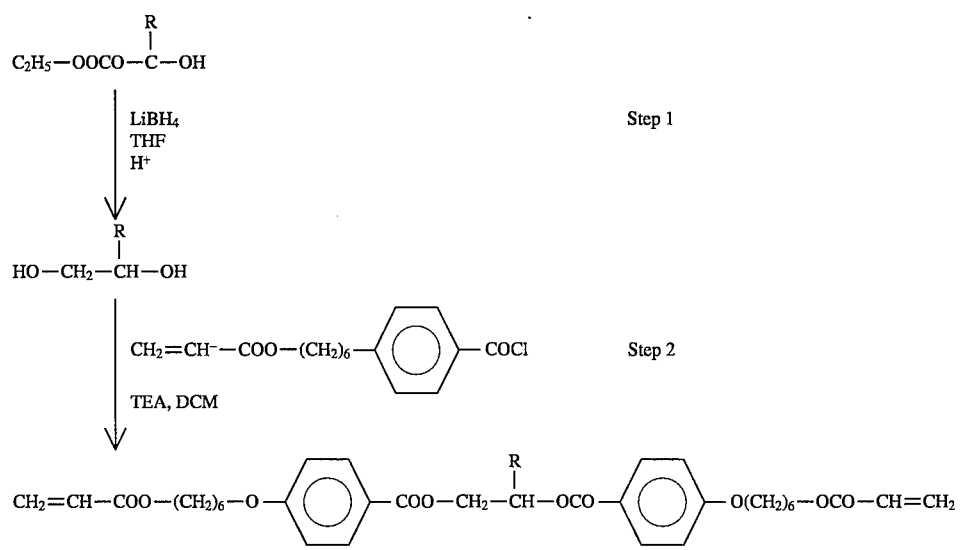
Scheme 8
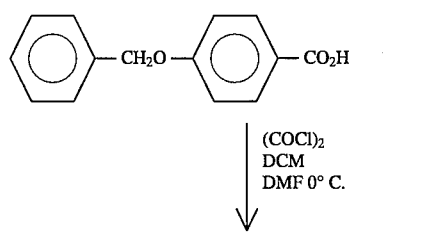

-continued
Scheme 8
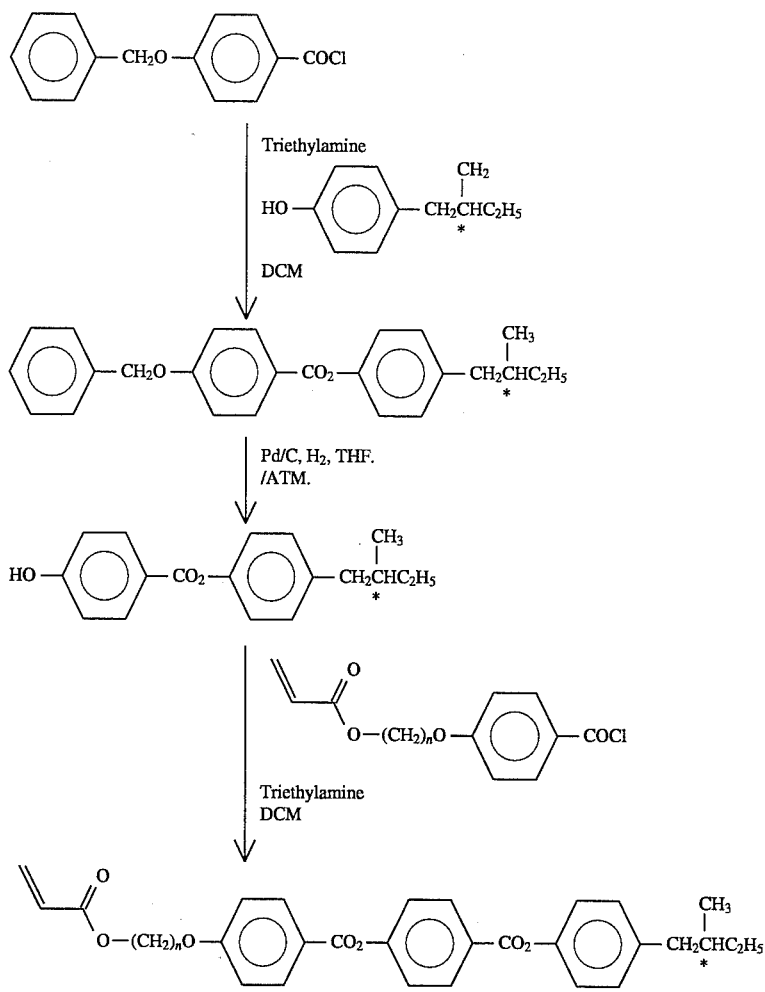
The preparation of peferred compounds is shown in the following, schemes 9 to 12 being 2 to 10, preferably 6.
Scheme 9
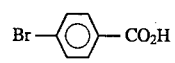
I.(COCl$_2$), DMF, DCM
II.Triethlamine, DCM
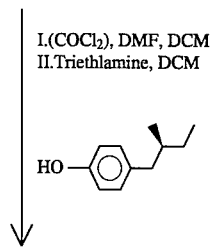

-continued
Scheme 9
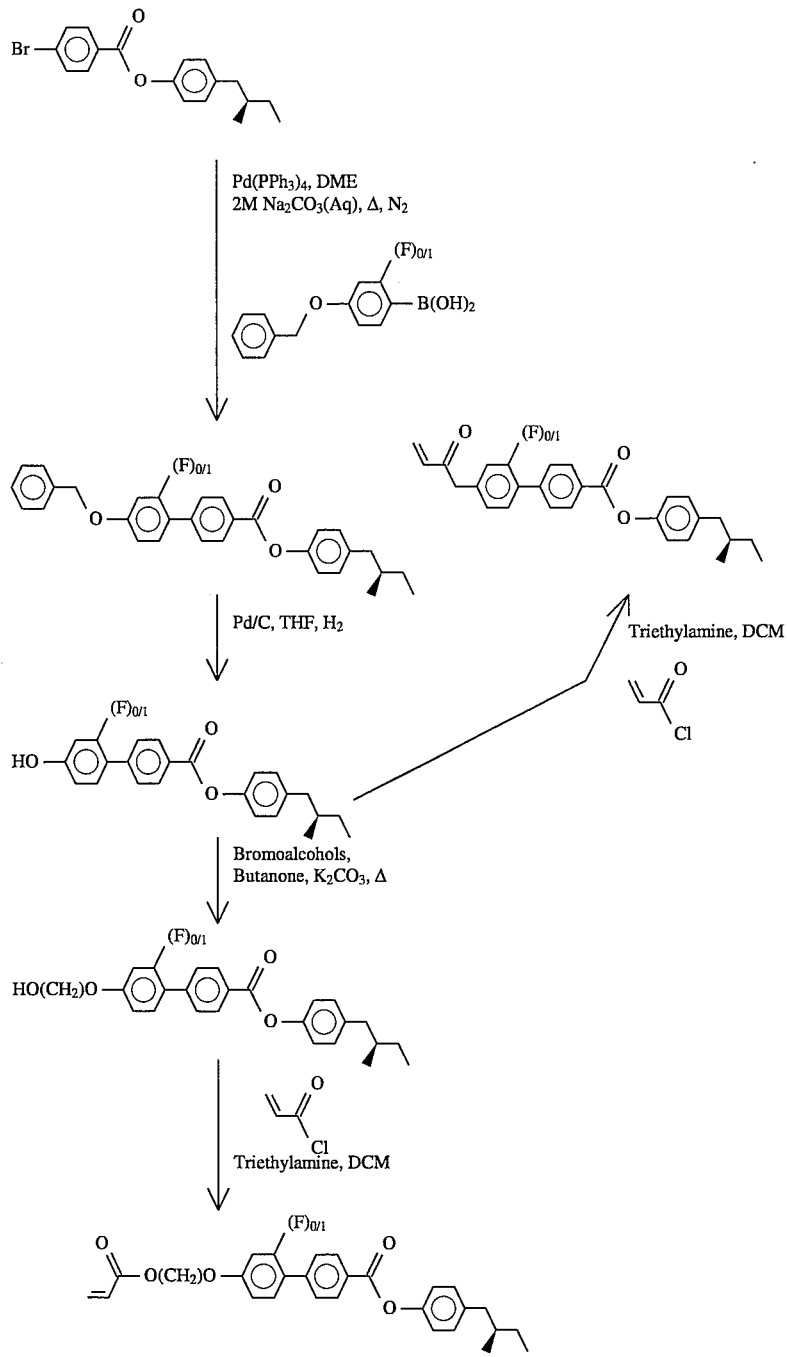

Scheme 10
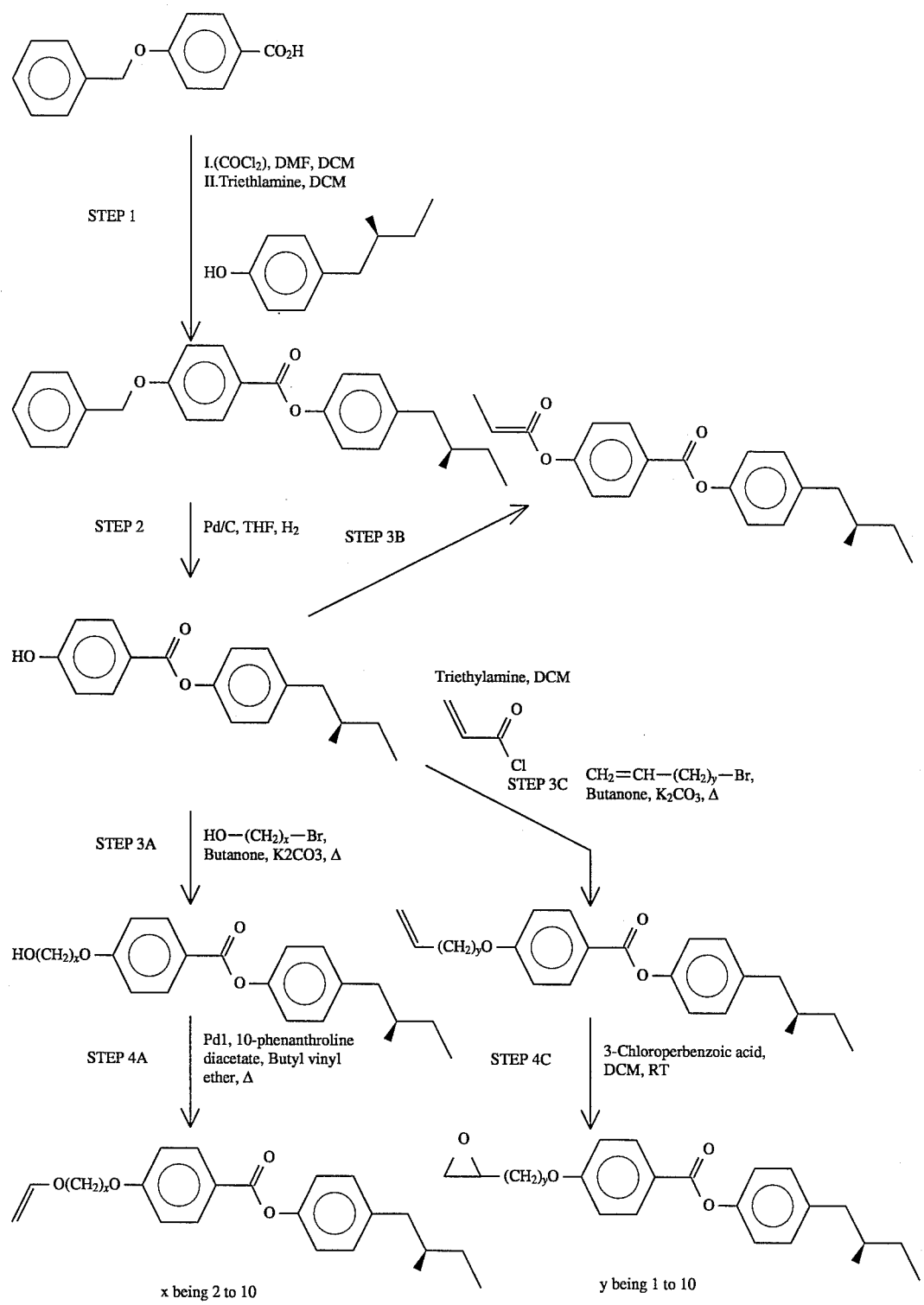

Scheme 11
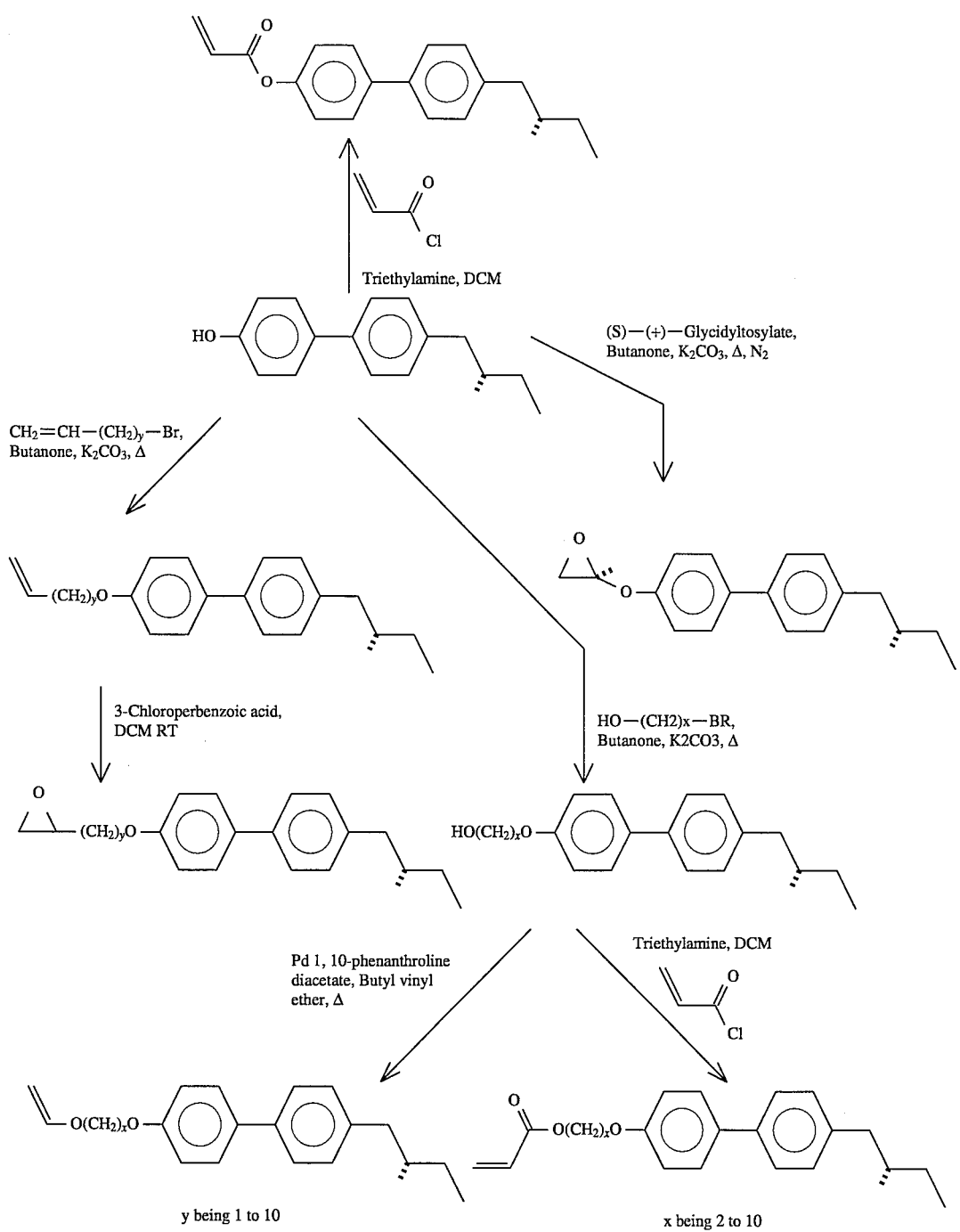
y being 1 to 10
x being 2 to 10

Scheme 12
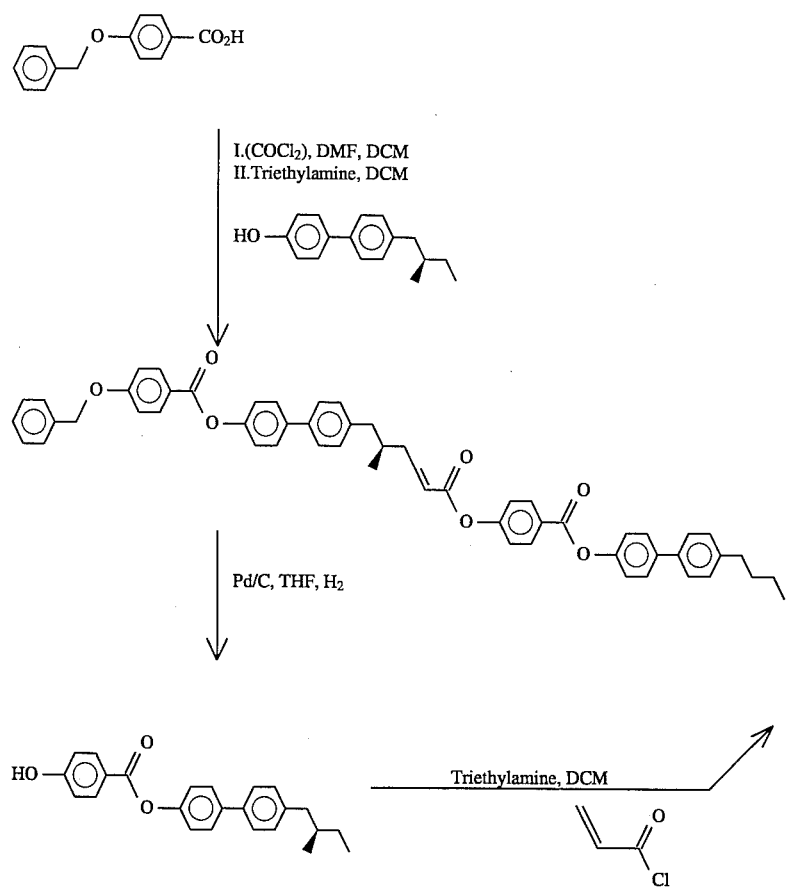

-continued
Scheme 12
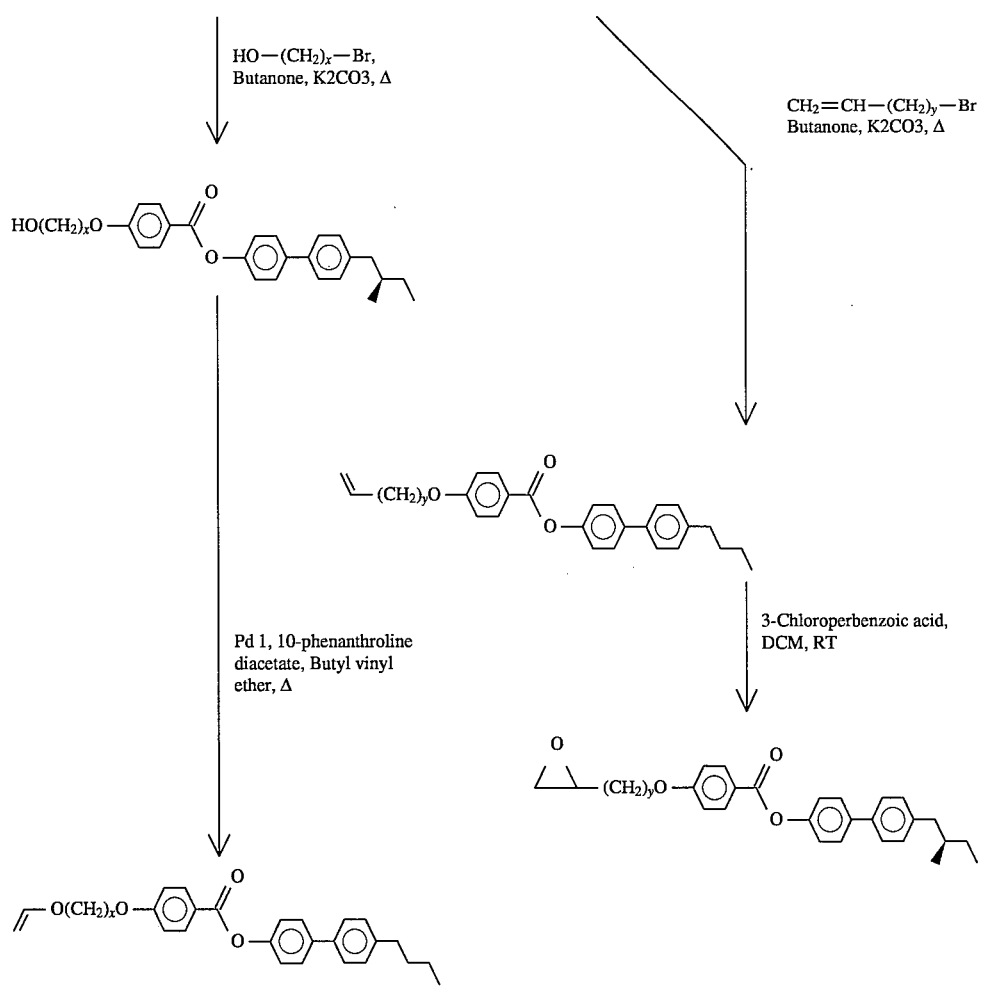

Scheme 13

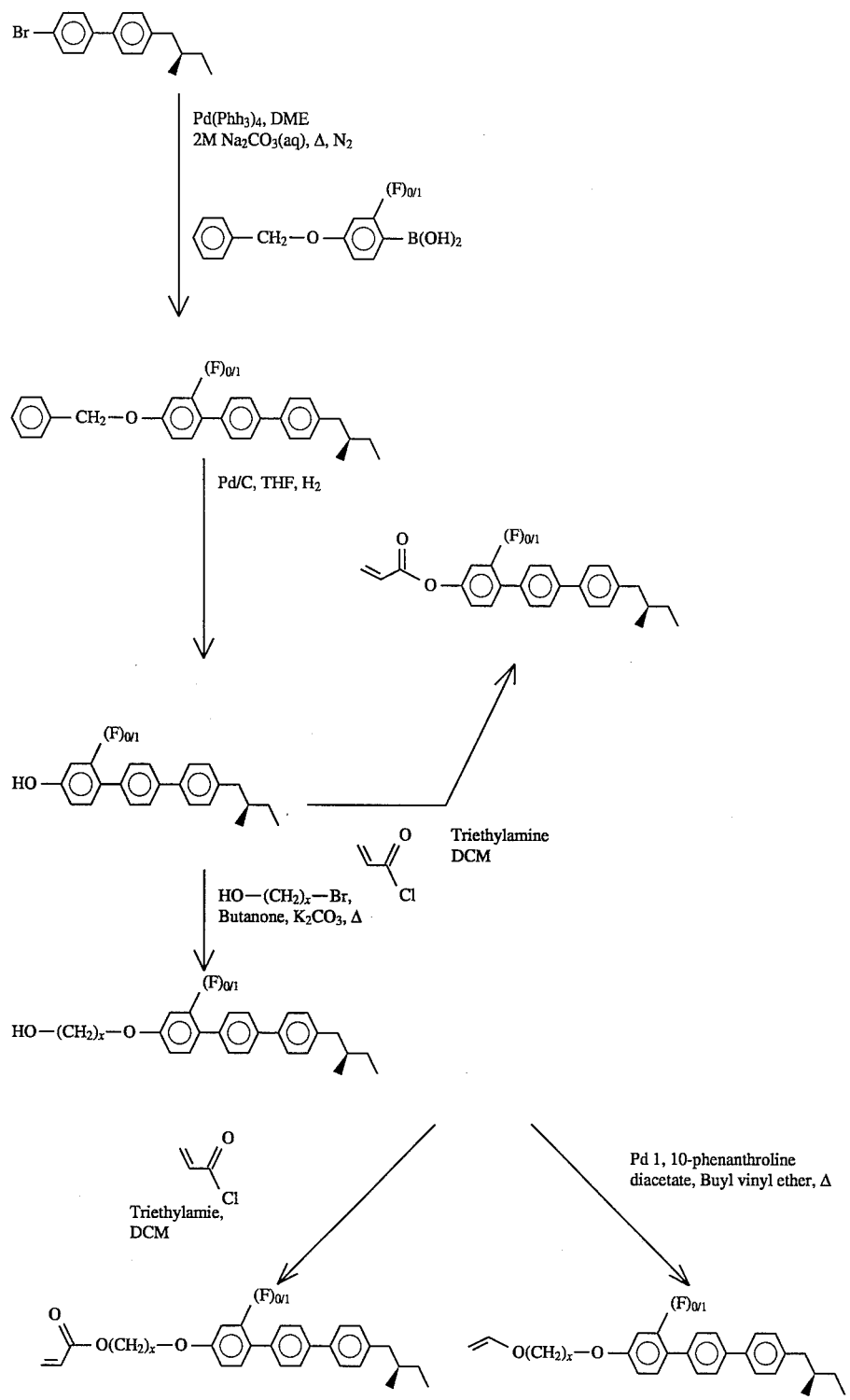

The inventive display exhibits two opposite plates which are transparent to light and which will hereinafter be termed substrates and which comprise electrodes on the opposing sides, said electrodes being manufactured from, for example, $In_2O_3 \cdot SnO_2$. On the electrode there is provided an orientation layer of, for example, rubbed polyimide or polyamide by means of which the liquid crystalline material according to the invention can be homogeneously aligned between the electrodes. The cell is manufactured by arranging the substrates thus formed and provided with electrodes closing the apertures by, for example, a ring-shaped member and filling the space between the substrates and the ring with the liquid-crystalline material according to the invention. In practice, a bonding layer of an epoxy compound can be used instead of the ring shown.

The liquid crystalline material can be capillary filled between two substrates which are provided with electrode layers, and then subsequently cured, for example, by irradiation with UV light, preferably in the presence of a photoinitiator, for example, an Irgacure®. Another possible but less attractive technique comprises coating of the LC material on a substrate with subsequent curing. The film may be peeled off and arranged between 2 substrates provided with electrode layers. It is also possible that the substrate onto which the LC material is applied exhibits an electrode layer so that the electrooptical system can be obtained by applying a second electrode layer and, optionally, a second substrate onto the coated and cured film.

The electrooptical system according to the invention can be operated reflectively or transmissively so that at least one electrode and, if present, the associated substrate are transparent. Both systems customarily contain no polarizers, as a result of which a distinctly higher light transmission results and is a considerable technological simplification in the production of these systems compared with conventional liquid crystal systems such as, for example, TN or STN cells.

In general a nematic liquid crystal mixture of positive dielectric anisotropy is desirable because these mixtures would be used in devices in which it is essential to electrically switch a thin film of such a mixture into a homeotropic alignment (field on state) and therefore appear clear to transparent, while the off state would usually be determined by the alignment within the cell, which is usually homogenous and this would give either a focal conic (slightly scattered) or grandjean (colored) state. It is possible that depending on how the voltage is applied or removed one can flip into either the colored grandjean or the slightly scattering focal conic state in the field on state. Moreover by adding a small amount of a liquid crystal material each state can be stabilized to give a bistable device with one stage being colored (grandjean texture) or essentially clear or slightly light scattering (focal conic). When placed against a black background a contrast between colored and black is clearly seen. The color being dependent on the pitch length of the cholesteric helix according to the equation $I_{max} = \bar{n} P \sin \Theta$ $\bar{n}$=mean refractive index of the LC, P=pitch length
$\Theta$=viewing angle.

The pitch length obtained when adding a chiral dopant to a nematic host depends on the polarizing ability of the LC molecules—the more polarizable they are the tighter the pitch length obtained (higher twisting power), so using a non-polar host may significantly alter how much chiral dopant would be needed to produce a given color.

Another application for this "blend" of chiral components is to mix them with reactive liquid crystals (for example of formula II) and produce a chiral colored reactive LC mixture which can be coated into a thin film and polymerized by UV light to give a thin polymer film which is colored. It would contain 20–30% nonreactive chiral LC as above, therefore, the polymer content is 70–80%.

The rise time increased accordingly as the cell thickness increases, but the decay time remains constant. The decay time decreases rapidly accordingly as the content of network molecules increases. Consequently, it is not the thickness of the cell that counts but the average distance between the network molecules. This explains the short decay times in comparison with the decay times (a few hundred milliseconds) in normal nematic cells. More particularly, decay times of a few milliseconds can be obtained.

The novel chiral reactive liquid crystalline compounds and compositions are highly suitable to produce cholesteric films which can be used in different optical and electrooptical applications.

Furthermore, they are useful as colored films for decorative applications. Since some of them show thermochromism, they can be used as temperature indicators, in particular as reversible or irreversible temperature indicators depending on their grade of polymerizations.

The invention will be explained in more detail by means of the following examples of the preparation of a liquid crystalline material according to the invention.

The mesogenic phases are abbreviated as following:

| K | crystalline |
|---|---|
| N | nematic |
| S | smectic |
| BP | blue phase |
| N* | chiral nematic (cholesteric) |
| HTP | helical twisting power |

In the foregoing and in the following examples, all temperatures are set forth uncorrected in degrees Celsius and unless otherwise indicated, all parts and percentages are by weight.

The entire disclosure of all applications, patents and publications, cited above and below, and of corresponding European application 94 102698.1, filed Feb. 23, 1994, are hereby incorporated by reference.

Example 1

The chiral reactive liquid crystalline compound (1)

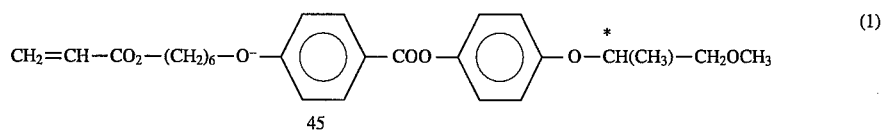

is prepared via the sequence of reaction steps shown in Scheme 1.

In step 6 of Scheme 1, 1 mol of the phenol obtained in step 5 and 1.1 mol of benzoyl chloride are dissolved in 1 l of dichlormethane. 1.1 mol of triethylamine are added, and the mixture is stirred for 3 hours at room temperature, K 50.8 ($S_A$-9) I.

Analogously are obtained:

| X* | n | Phase transition [°C.] |
|---|---|---|

CH₂=CH—CO—O—(CH₂)ₙ—O—⟨phenyl⟩—COO—⟨phenyl⟩—X*

| X* | n | Phase transition [°C.] |
|---|---|---|
| —OCH*(CH₃)—CH₂—OCH₃ | 4 | K 34 I |
| —OCH*(CH₃)—CH₂—OCH₃ | 2 | K 73 I |
| —OCH*(CH₃)—C₆H₁₃ | 6 | K 55 (S$_A$-4) I |
| —OCH*(CH₃)—C₆H₁₃ | 4 | K 30 I |
| —OCH*(CH₃)—C₆H₁₃ | 2 | K 65 I |
| —OCH*(CH₃)—C₂H₅ | 6 | K 67 (S$_A$-8) I |
| —OCH*(CH₃)—C₂H₅ | 4 | K 43.5 I |
| —OCH*(CH₃)—C₂H₅ | 2 | K 64 I |
| —CH₂CH*(CH₃)—C₂H₅ | 6 | K 35 (S$_A$-8) I |
| —CH₂CH*(CH₃)—C₂H₅ | 5 | K 38 (S$_A$ + 1.5) I |
| —CH₂CH*(CH₃)—C₂H₅ | 4 | K 44 I |
| —CH₂CH*(CH₃)—C₂H₅ | 3 | K 48 I |
| —CH₂CH*(CH₃)—C₂H₅ | 2 | K 51 I |

CH₂=CH—O—(CH₂)ₙ—O—⟨phenyl⟩—COO—⟨phenyl⟩—X*

| X* | n | Phase transition [°C.] |
|---|---|---|
| —OCH*(CH₃)—CH₂—OCH₃ | 6 | |
| —CH₂—CH*(CH₃)—C₂H₅ | 6 | K 52 (S$_A$ 31.8 N* 37,6) I |
| —CH₂—CH*(CH₃)—C₂H₅ | 4 | |
| —CH₂—CH*(CH₃)—C₂H₅ | 2 | |

CH₂=CH—COO—(CH₂)ₙ—O—⟨phenyl⟩—COO—⟨phenyl⟩—⟨phenyl⟩—X*

| X* | n | Phase transition [°C.] |
|---|---|---|
| —CH₂—CH*(CH₃)—C₂H₅ | 6 | K 81 (S 65) N* 131 BP 131.3 I |
| —CH₂—CH*(CH₃)—C₂H₅ | 5 | K 74 (S 59.3) N* 138.8 BP 139.2 |
| —CH₂—CH*(CH₃)—C₂H₅ | 4 | K 89.5 (S 56.5) N* 135.3 BP 135.9 I |
| —CH₂—CH*(CH₃)—C₂H₅ | 3 | K 87 (S 60) N* 142.8 BP 143.2 |
| —CH₂—CH*(CH₃)—C₂H₅ | 2 | K 86 (S 55,7) N* 125.2 BP 125.7 I |
| —OCH*(CH₃)—CH₂OCH₃ | 6 | |

CH₂=CH—COO—(CH₂)ₙ—O—⟨phenyl⟩—COO—⟨phenyl⟩—COO—⟨phenyl⟩—CH₂—CH*(CH₃)—C₂H₅

(prepared according to Scheme 8)

| n | Phase transition [°C.] |
|---|---|
| 2 | |
| 4 | |
| 6 | K 83 SA 108.8 N* 139.5 BP 139.8 I |

$$CH_2=CH-CO-O-MG^1-\underset{\ast}{\bigcirc}-CH_2-\overset{\ast}{C}H(CH_3)-C_2H_5$$

(prepared according to Schemes 9 to 12)

| $MG^1$ | Phase transition | HTP |
|---|---|---|
| ![biphenyl-COO] | K 94 (S 79) $S_A$ 143 N* 154 BP 154.7 I | 4.31 |
| ![fluoro-biphenyl-COO] | K 126 N* 221.9 (BP 220) I | 4.63 |
| ![phenyl-COO] | K 43 (N* 18) I | 6.95 |
| ![phenyl] | K 38 I | 6.80 |
| ![phenyl-COO-phenyl] | K 109 N* 204 I | 5.19 |

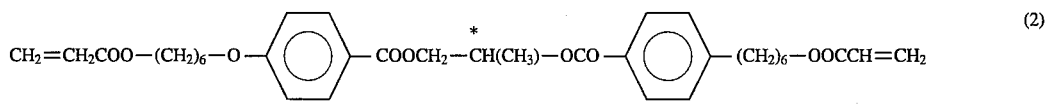

(prepared according to Scheme 13)
K 67.4 $S_A$ 92 N* 135 I

Example 2

The chiral reactive liquid crystalline compound (2)

$$CH_2=CH_2COO-(CH_2)_6-O-\bigcirc-COOCH_2-\overset{\ast}{C}H(CH_3)-OCO-\bigcirc-(CH_2)_6-OOCCH=CH_2 \quad (2)$$

is prepared via the sequence of reaction steps shown in Scheme 7 and exhibits the following phase sequence K 31 I.

DCM is dichloromethane

In step 2 of Scheme 7 2.2 mol of triethylamine is added dropwise to a solution of 1 mol of the (S)-(−)-1,2 propandiol and 2.1 mol acryloyloxy hexyloxy benzoyl chloride in 2 l dichloromethane. It is stirred for 4 hours at room temperature. Aqueous work-up and column chromatography gives (2).

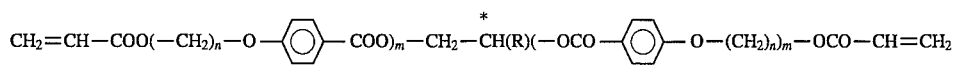

| n | m | R |
|---|---|---|
| 6 | 1 | C$_6$H$_5$, K59.11 |
| – | 0 | C$_6$H$_5$ liquid |

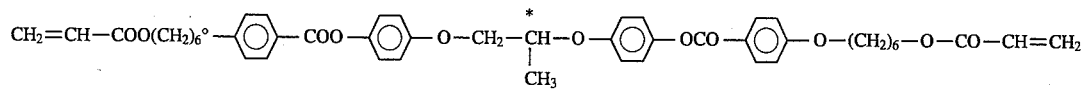

Example 3

The reactive liquid crystalline compound (3)

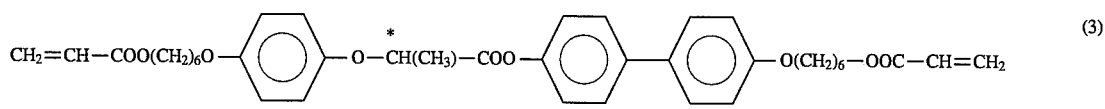
(3)

is prepared via the sequence of reaction steps shown in Schemes 5 and 6.

In step 2 of Scheme 6, 2.2 mol triethylamine is added dropwise to a solution of the ester obtained in step 1 of Scheme 6, and 2.1 mol acryloyl chloride in 2 l dichloromethane. The reaction mixture is stirred at room temperature for 4 hours. Aqueous workup and column chromatography gives (3),
the following compound is prepared analogously.

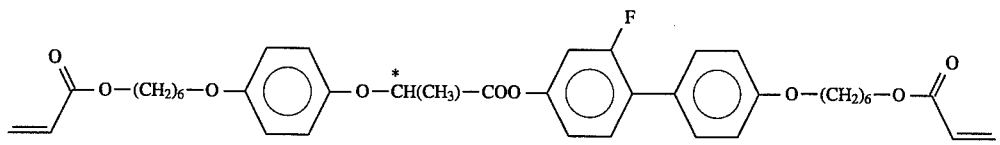
(3.1)

Example 4

A mixture is formulated consisting of

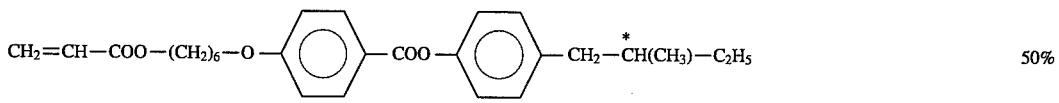 50%

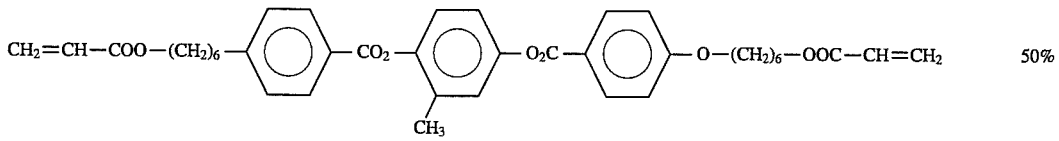 50% exhibits K 40 Ch 59 I and reflects selectivity with a wavelength of maximum reflection of 580 nm 0.467% by weight of a photoinitiator (coded KB 1) are added and the resulting mixture is aligned on rubbed PVA unidirectionally with 0.5% by weight of 16 μm spacers and is photopolymerized to achieve full polymerization and to give a chiral polymeric network with a selective reflection maximum of 580 nm.

Example 5

A mixture is formulated consisting of

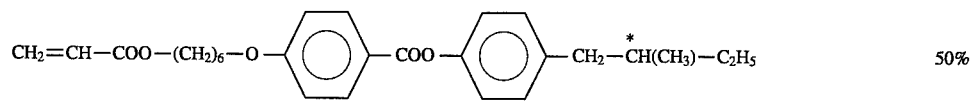 50%

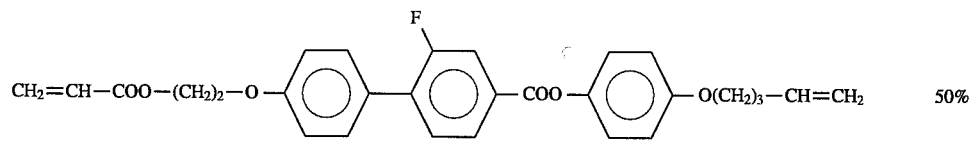 50% exhibits K 16 Ch 62 I, relfects selectively at 580 nm and is aligned as shown in Example 4 before photopolymerization.

Example 6

A mixture is formulated consisting of

| Structure | % |
|---|---|
| CH$_2$=CH—COO—(CH$_2$)$_2$—O—⟨○⟩—COO—⟨○⟩—CH$_2$*CH(CH$_3$)—C$_2$H$_5$ | 24.96% |
| CH$_2$=CH—COO—(CH$_2$)$_6$—O—⟨○⟩—COO—⟨○⟩—COO—⟨○⟩—CH$_2$*CH(CH$_3$)—C$_2$H$_5$ | 24.98% |
| CH$_2$=CH—COO—(CH$_2$)$_6$—O—⟨○⟩—COO—⟨○⟩(CH$_3$)—OCO—⟨○⟩—O—(CH$_2$)$_6$—OCO—CH=CH$_2$ | 49.55% |
| photoinitiator | 0.5% | exhibits K 52-68 Ch 90-5 I and appears green.

Example 7

A mixture is formulated consisting of

| Structure | % |
|---|---|
| CH$_2$=CH—COO—(CH$_2$)$_6$—O—⟨○⟩—COO—⟨○⟩—CH$_2$*CH(CH$_3$)—C$_2$H$_5$ | 50% |
| CH$_2$=CH—COO—(CH$_2$)$_6$—O—⟨○⟩—COO—⟨○⟩—OCO—⟨○⟩—O—(CH$_2$)$_6$—OCO—CH=CH$_2$ | 50% | and appears green.

Example 8

A mixture is formulated consisting of

| Structure | % |
|---|---|
| CH$_2$=C(CH$_3$)—COO—(CH$_2$)$_6$—O—⟨○⟩—COO—⟨○⟩(CH$_3$)—OCO—⟨○⟩—O—(CH$_2$)$_6$—O—CO—C(CH$_3$)=CH$_2$ | 50% |
| CH$_2$=CH—COO—⟨○⟩—COO—⟨○⟩—CH$_2$*CH(CH$_3$)—C$_2$H$_5$ | 50% |

K 45 N* 61 I    $\lambda_{max}$ = 530 nm

Supercools to room temperature and slowly over 3 days.

Example 9

A mixture is formulated consisting of

| Structure | % |
|---|---|
| CH$_2$=CH—O—(CH$_2$)$_4$—O—⟨○⟩—⟨○⟩(Cl)—⟨○⟩—O—(CH$_2$)$_4$—OCH=CH$_2$ | 50% |
| CH$_2$=CH—O—(CH$_2$)$_4$—O—⟨○⟩—⟨○⟩—⟨○⟩—CH$_2$*CH(CH$_3$)—C$_2$H$_5$ | 50% |

K 38-68 (N* 50) I    $\lambda_{max}$ = 540 nm

Supercools to toom temperature and crystallizes slowly over 3 days.

Example 10

A mixture is formulated consisting of

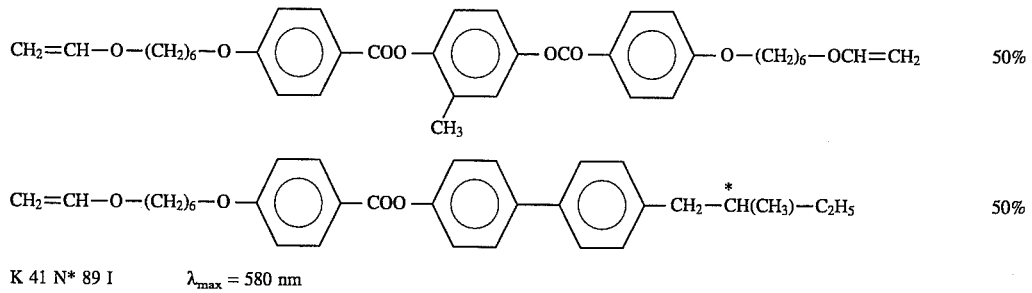 50%

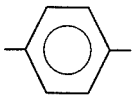 50%

K 41 N* 89 I   $\lambda_{max} = 580$ nm

Supercools to 0° C. and crystallizes overnight.

Example 11

The chiral reactive liquid crystalline compound (3)

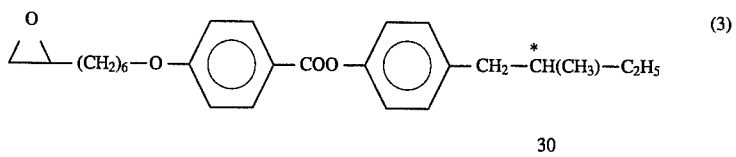 (3)

is prepared via the sequence of reaction steps in Scheme 10.

In step 4C of Scheme 10 1 mol of 4-(2-methylbutyl)phenyl 4-oct-7 enylbenzoate obtained in step 3C and 1.1 mol 3-chloroperbenzoic acid are dissolved in 1 l of dichloromethane and stirred for 3 hours at room temperature. The resulting product shows K 29 (N* 26.3) I and HTP=4.56.

Analogously are obtained:

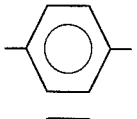

| n | MG¹ | phase transitions (°C.) | HTP |
|---|---|---|---|
| 1 | 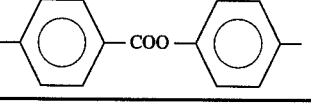 | K 67 I | 5.73 |
| 3 | 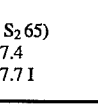 | K 48 I | 6.25 |
| 6 | —⬡—COO—⬡— | K 74 (S₁ 41 S₂ 65) N* 157.4 BP 157.7 I | 4.21 |

Example 12

A mixture is formulated consisting of

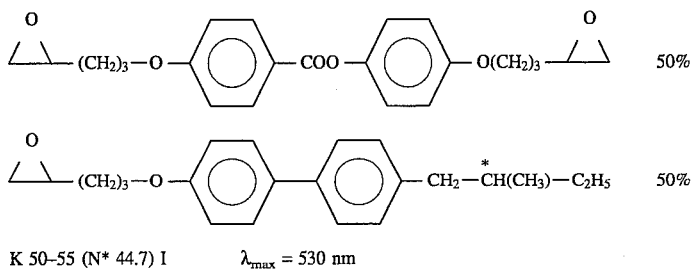

K 50–55 (N* 44.7) I    $\lambda_{max}$ = 530 nm

Supercools to room temperature and crystallizes slowly over 3 days.

Example 13

A mixture is formulated consisting of

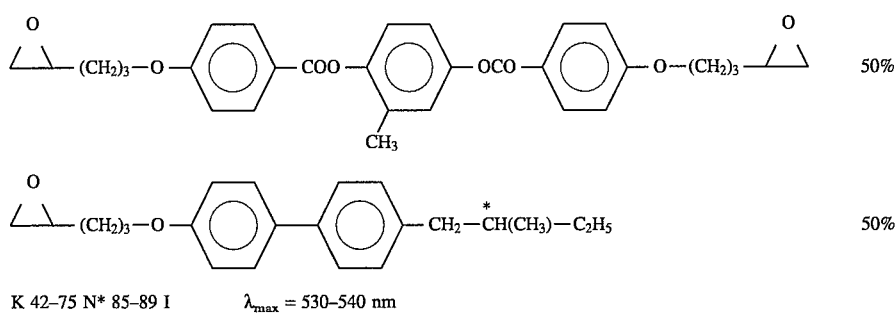

K 42–75 N* 85–89 I    $\lambda_{max}$ = 530–540 nm

Supercools to room temperature and crystallizes overnight.

Example 14

A mixture is formulated consisting of

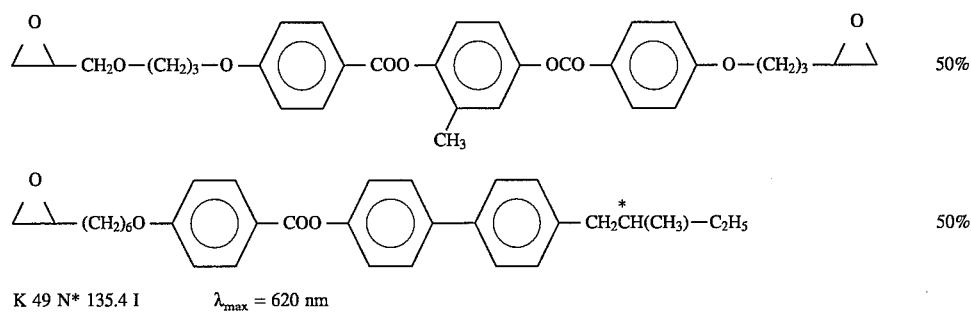

K 49 N* 135.4 I    $\lambda_{max}$ = 620 nm

Supercools to room temperature and crystallizes overnight.

Example 15

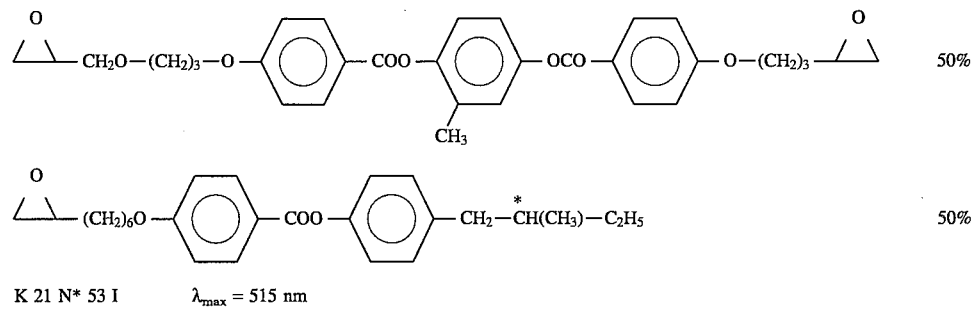

K 21 N* 53 I    $\lambda_{max}$ = 515 nm

Supercools to room temperature without crystallization.

What is claimed is:

1. A copolymerizable precursor material comprising at least one bifunctional reactive achiral compound of formula VI $$R^4—(P)_u—MG^1—(P)_u—R^4 \qquad VI$$

and at least one mono reactive chiral compound of formula I

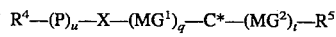

wherein $R^4$ is $CH_2=CW-COO-$,

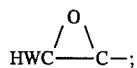

$HWN-$, $CH_2=CH-$, $CH_2=CH-O-$ or $HS-CH_2-(CH_2)_m-COO-$ with W being H, Cl or alkyl with 1-5 C atoms and m being 1-7, P is alkylene with 1 to 12 C atoms, optionally, with one or more non-adjacent $CH_2$ groups replaced by $-O-$, X is $-O-$, $-S-$, $-COO-$, $-OCO-$ or a single bond, $R^5$ is an alkyl radical with 1 to 15 C atoms which is unsubstituted or mono- or polysubstituted by halogen, optionally with one or more CH groups replaced, in each case independently of one another, by $-O-$, $-S-$, $-CO-$, $-OCO-$, $-CO-O-$ or $-O-CO-O-$ in such a manner that oxygen atoms are not linked directly to one another, or alternatively $R^5$ has one of the meanings given for $R^4-(P)_u-X-$, $MG^1$ and $MG^2$ are each independently a mesogenic group comprising an aromatic ring system or two or more ring systems optionally linked by bridging groups, C* is an optically active group, q an t are each independently 0 or 1 provided that q+t is 1 or 2, and u is 0 or 1.

2. A copolymerizable precursor material according to claim 1, wherein in at least one reactive chiral compound of formula I

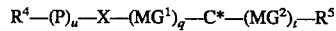

$R^4$ is an acrylate radical of formula

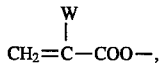

wherein W is H, Cl or alkyl of 1-5 C atoms.

3. A copolymerizable precursor material according to claim 1, wherein in at least one compound of formula I $R^4$ is a vinyl ether radical of formula $CH_2=CH-O-$.

4. A copolymerizable precursor of claim 1, wherein the monoreactive chiral compound is selected from one of the formulae III to V

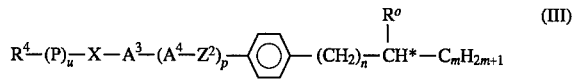

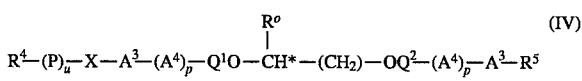

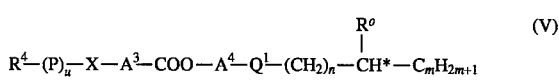

wherein $R^4$, X, P, $R^5$ and u have the meaning given, $A^3$ and $A^4$ are each independently optionally fluorinated 1,4-phenylene in which one or two CH groups may be replaced by N or 1,4-cyclohexylene in which one or two non-adjacent $CH_2$ groups may be replaced by O, $Z^2$ is $-CO-O$, $-O-CO-$, $-OCH_2-$, $-CH_2O-$, $-CH_2CH_2-$, $-C\equiv C-$, $-C\equiv C-C\equiv C-$ or a single bond, and p is 0, 1 or 2, $R^o$ is $CH_3$, $C_6H_5$, F, Cl, CN or $CF_3$, $Q^1$ and $Q^2$ are each, independently, CO or a single bond, n is 0, 1 or 2, and m is an integer of 1 to 10.

5. A cholesteric film obtained by the steps comprising a) ordering the copolyermizable precursor material of claim 1 in the monomeric state in the presence of a UV initiator and optionally an additive, and b) in situ UV polymerizing the resulting ordered precursor material.

6. The copolymerizable precursor of claim 4, wherein $R^o$ is $CH_3$ or $C_6H_5$.

7. The copolymerizable precursor of claim 1, wherein, in the chiral compound of formula I, C* is a group selected from one of the following formulae:

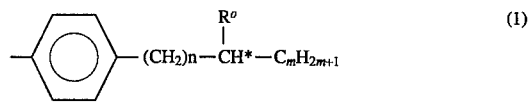

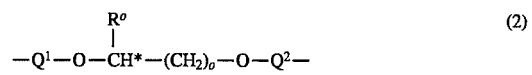

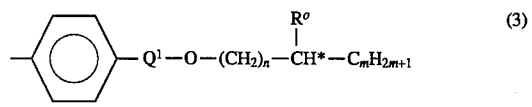

wherein $R^o$ is $CH_3$, $C_6H_5$, F, Cl, CN or $CF_3$, $Q^1$ and $Q^2$ are each, independently CO or a single bond, n is 0, 1 or 2, m is an integer from 1 to 10, o is 1, 2 or 3, and

* denotes a chiral center.

8. The copolymerizable precursor of claim 7, wherein C* is a group of formula (2) or (4).

9. The copolymerizable precursor of claim 1, wherein, in the achiral compound of formula VI and the chiral compound of formula I, $MG^1$ and $MG^2$ are, independently, selected from groups of the following formulae:

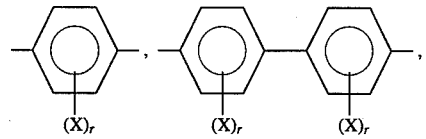

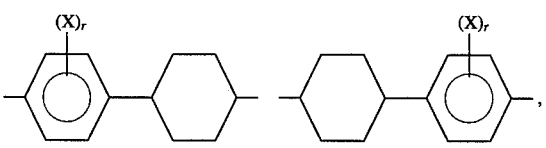

-continued

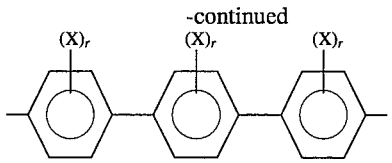

wherein X is CN or F and r is 0, 1 or 2.

10. The copolymerizable precursor of claim 4, wherein the chiral compound is of the formula (III), wherein n is 1, m is 2 and $R^o$ is $CH_3$.

11. The copolymerizable precursor of claim 1, wherein the chiral compound is present in a quantity of 1–50% by weight.

12. The copolymerizable precursor of claim 1, wherein the chiral compound is present in a quantity of 2–10% by weight.

13. A monofunctional reactive compound of formula IIIa

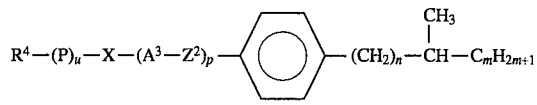

in which $R^4$ is $CH_2$=CW—COO—,

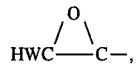

HWN—, $CH_2$=CH—, $CH_2$=CH—O— or HS—$CH_2$—$(CH_2)_m$—COO— with W being H, Cl or alkyl with 1–5 C atoms and m being 1–7, P is alkylene with 1 to 12 C atoms, optionally, with one or more non-adjacent $CH_2$ groups replaced by —O—, X is —O—, —S—, —COO—, —OCO— or a single bond, u is 0 or 1, $A^3$ is optionally fluorinated 1,4-phenylene in which one or two CH groups may be replaced by N or 1,4-cyclohexylene in which one or two non-adjacent $CH_2$ groups may be replaced by O, $Z^2$ is —CO—O—, —O—CO—, —OCH_2—, —CH_2O—, —CH_2CH_2—, —C≡C—, —C≡C—C≡C—, or a single bond, n is 0 or an integer of 1 to 20, p is 1 or 2, and m is an integer of from 2 to 10.

14. The monofunctional reactive compound of claim 13, in which n is 1 and m is 2.

* * * * *